(12) United States Patent
Kozbor et al.

(10) Patent No.: US 7,011,845 B2
(45) Date of Patent: Mar. 14, 2006

(54) β-GLUCANS ENCAPSULATED IN LIPOSOMES

(75) Inventors: Danuta Kozbor, Philadelphia, PA (US); Yutaro Kaneko, Tokyo (JP)

(73) Assignees: MCP Hahnemann University, Philadelphia, PA (US); Ajinomoto Co., Inc., Tokyo (JP)

(*) Notice: Subject to any disclaimer, the term of this patent is extended or adjusted under 35 U.S.C. 154(b) by 0 days.

(21) Appl. No.: 09/566,993

(22) Filed: May 9, 2000

(65) Prior Publication Data

US 2002/0146448 A1 Oct. 10, 2002

(51) Int. Cl.
*A61K 9/127* (2006.01)

(52) U.S. Cl. .................. 424/450; 424/435; 514/23; 514/25

(58) Field of Classification Search ................ 620/652; 514/23, 25; 424/430, 433, 434, 435, 436, 424/450
See application file for complete search history.

(56) References Cited

U.S. PATENT DOCUMENTS

| | | | | |
|---|---|---|---|---|
| 4,971,956 A | * | 11/1990 | Suzuki ................. | 514/55 |
| 5,504,079 A | * | 4/1996 | Jamas | |
| 5,512,672 A | * | 4/1996 | Yamamoto | |
| 5,762,904 A | * | 6/1998 | Okada et al. ........... | 424/1.21 |
| 5,925,362 A | * | 7/1999 | Spilter ................ | 424/277.1 |
| 6,060,082 A | * | 5/2000 | Chen et al. ............ | 424/450 |
| 6,090,406 A | * | 7/2000 | Popescu et al. ........ | 424/450 |
| 6,207,185 B1 | * | 3/2001 | See et al. ............. | 424/450 |
| 6,355,414 B1 | * | 3/2002 | Rubido | |

OTHER PUBLICATIONS

Wassey Immunomethods 4, p 217-222, 1994.*

Tazawa J. Exp. Clin. Can. Res. 11 p. 21-28, 1992.*

V. Vetvicka, et al., The Journal of Immunology, pp. 599-605, Targeting of Natural Killer Cells to Mammary Carcinoma via Naturally Occuring Tumor Cell-Bound iC3b and β-Glucan-Primed CR3 (CD11b/CD18), 1997.

V. Vetvicka, et al., J. Clin. Invest., vol. 98, No. 1, pp. 50-61, "Soluble β-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells", Jul. 1996.

I. C. Diller, et al., Cancer Research, vol. 23, pp. 201-208 (with Figs. 5 and 6), "The Effect of Yeast Polysaccharides on Mouse Tumors", Feb. 1963.

N. R. Di Luzio, et al., Int. J. Cancer, vol. 24, pp. 773-779, "Comparative Tumor-Inhibitory and Anti-Bacterial Activity of Soluble and Particulate Glucan", 1979.

R. Seljelid, et al., Immunopharmacology, vol. 7, pp. 69-73, "A Soluble β-1,3-D-Glucan Derivative Potentiates the Cytostatic and Cytolytic Capacity of Mouse Peritoneal Macrophages in vitro", 1984.

K. Morikawa, et al., Cancer Research, vol. 46, pp. 66-70, "Calcium-Dependent and -Independent Tumoricidal Activities of Polymorphonuclear Leukocytes Induced by a Linear β-1,3-D-Glucan and Phorbol Myristate Acetate in Mice[1]", Jan. 1986.

J. Hamuro, et al., Cancer Research, vol. 38, pp. 3080-3085, "β(1-3) Glucan-Mediated Augmentation of Alloreactive Murine Cytotoxic T-Lymphocytes in vivo[1]", Sep. 1978.

(Continued)

*Primary Examiner*—Gollamudi S. Kishore
(74) *Attorney, Agent, or Firm*—Oblon, Spivak, McClelland, Maier & Neustadt, P.C.

(57) ABSTRACT

Liposomes encapsulating a β-glucan have an improved activity of enhancing a cellular immunity, especially when they are transmucosally administered. Thus, the liposomes are useful for the treatment or prevention of infection or tumor.

13 Claims, 5 Drawing Sheets

OTHER PUBLICATIONS

G. D. Ross, Clinical Aspects of Immunology, vol. 1, No. 5, pp. 241-264, "Membrane Complement Receptors", 1993.

A. Estrada, et al., Microbiol. Immunol., vol. 41, No. 12, pp. 991-998, "Immunomodulatory Activities of Oat β-Glucan in vitro and in vivo", 1997.

H. Matsuoka, et al., Anticancer Research, vol. 17, pp. 2751-2756, "Lentinan Potentiates Immunity and Prolongs the Survival Time of Some Patients", 1997.

Y. Kaneko, et al., Microbial Infections, pp. 201-215, "Potentiation of Host Resistance Against Microbial Infections by Lentinan and its Related Polysaccharides", 1992.

G. Chihara, Immunotherapeutic Prospects of Infectious Diseases, pp. 9-18, "Lentinan and its Related Polysaccharides as Host Defence Potentiators: Their Application to Infectious Diseases and Cancer", 1990.

T. Taguchi, et al., Adv. Exp. Med. Biol., vol. 166, pp. 181-187, Clinical Efficacy of Lentinan on Neoplastic Diseases, 1983.

K. Tari, et al., Acta Urol. Jpn., vol. 40, pp. 119-123, "Effect of Lentinan for Advanced Prostate Carcinoma", 1994 (with partial English translation).

S. Fujimoto, et al., Japanese Journal of Surgery, vol. 14, No. 4, pp. 286-292, "Clinical Evaluation of Schizophyllan Adjuvant Immunochemotherapy for Patients with Resectable Gastric Cancer a Randomized Controlled Trial", 1984.

D. H. Jones, et al., Vaccine, vol. 15, No. 8, pp. 814-817, "Poly(DL-Lactide-CO-Glycolide)-Encapsulated Plasmid DNA Elicits Systemic and Mucosal Antibody Responses to Encoded Protein After Oral Administration", 1997.

S. C. Chen, et al., Journal of Virology, vol. 72, No. 7, pp. 5757-5761, "Protective Immunity Induced by Oral Immunization with a Rotavirus DNA Vaccine Encapsulated in Microparticles", Jul. 1998.

H. Kaneko, et al., Virology, vol. 267, pp. 8-16, "Oral DNA Vaccination Promotes Mucosal and Systemic Immune Responses to HIV Envelope Glycoprotein", 2000.

M. L. Hedley, et al., Nature Medicine, vol. 4, No. 3, pp. 365-368, "Microspheres Containing Plasmid-Encoded Antigens Elicit Cytotoxic T-Cell Responses", Mar. 1998.

B. S. Bender, et al., Journal of Virology, vol. 70, No. 9, pp. 6418-6424, "Oral Immunization with a Replication-Deficient Recombinant Vaccinia Virus Protects Mice Against Influenza", Sep. 1996.

M. M. Gherardi, et al., Vaccine, vol. 17, pp. 1074-1083, "Mucosal and Systemic Immune Responses Induced After Oral Delivery of Vaccinia Virus Recombinants", 1999.

P. L. Earl, et al., Journal of Virology, vol. 65, No. 1, pp. 31-41, "Biological and Immunological Properties of Human Immunodeficiency Virus Type 1 Envelope Glycoprotein: Analysis of Proteins with Truncations and Deletions Expressed by Recombinant Vaccinia Viruses", Jan. 1991.

M. Mackett, et al., Proc. Natl. Acad. Sci. USA, vol. 79, pp. 7415-7419, "Vaccinia Virus: A Selectable Eukaryotic Cloning and Expression Vector", Dec. 1982.

B. Moss, et al., Nature, vol. 311, No. 6, pp. 67-69, "Live Recombinant Vaccinia Virus Protects Chimpanzees Against Hepatitis B", Sep. 6, 1984.

G. Gregoriadis, et al., Eur. J. Biochem., vol. 24, No. 3, pp. 485-491, "Fate of Protein-Containing Liposomes Injected into Rats", 1972.

P. L. Felgner, et al., Annals New York Academy Sciences, pp. 126-139, "Improved Cationic Lipid Formulations for in vivo Gene Therapy", 1996.

I. M. Belyakov, et al., Proc. Natl. Acad. Sci. USA, vol. 95, pp. 1709-1714, "Mucosal Immunization with HIV-1 Peptide Vaccine Induces Mucosal and Systemic Cytotoxic T Lymphocytes and Protective Immunity in Mice Against Intrarectal Recombinant HIV-Vaccinia Challenge", Feb. 1998.

D. H. Barouch, et al., The Journal of Immunology, pp. 1875-1882, "Augmentation and Suppression of Immune Responses to an HIV-1 DNA Vaccine by Plasmid Cytokine/IG Administration[1]", 1998.

H. F. Staats, et al., The Journal of Immunology, pp. 462-472, "Mucosal Immunity to HIV-1", 1996.

H. Takahashi, et al., The Journal of Experimental Medicine, vol. 183, pp. 879-889, "Inactivation of Human Immunodeficiency Virus (HIV)-1 Envelope-Specific CD8+ Cytotoxic T Lymphocytes by Free Antigenic Peptide: A Self-Veto Mechanism?", Mar. 1996.

K. Tazawa, et al., J. Exp. Chin. Cancer Res., vol. 11, No. 1, pps. 21-28, "Inhibitory Effect of Lentinan Entrapped in Liposomes on Pulmonary Metastasis in Rats. Distribution of Liposomes and Enhancement of NK Cell Activity," 1992.

N.M. Wassef, et al., Immunomethods, vol. 4, pps. 217-222, "Liposomes as Carriers for Vaccines," 1994.

T.F. Kresina, et al., "Human Immunodificiency Virus Type 1 Infection, Mucosal Immunity, and Pathogenesis and Extramural Research Programs at the National Institutes of Health", The Journal of Infectious Diseases, 179 (Suppl 3), 1999, pp. S392-S396.

S. Lucchini, et al., "Broad-Range Bacteriophage Resistance in Streptococcus thermophilus by Insertional Mutagenesis", Virology, 275, 2000, pp. 267-277.

E. Sheu, et al., "The Gene Pill and its Therapeutic Applications", Current Opinion in Molecular Therapeutics, vol. 5, No. 4, 2003, pp. 420-427.

A. Wierzbicki, et al., "Immunization Strategies to Augment Oral Vaccination with DNA and Viral Vectors Expressing HIV Envelope Glycoprotein", Vaccine, 20, 2002, pp. 1295-1306.

* cited by examiner

A

B

A

B

β-GLUCANS ENCAPSULATED IN LIPOSOMES

FIELD OF THE INVENTION

The present invention relates to liposomes encapsulating a β-glucan. The liposomes strongly enhance cellular immune responses, especially when transmucosally administered. Thus, they can be used as adjuvants used in combination with vaccines (antigens). Due to their high activities of enhancing a cellular immunity, the liposomes are useful also for the treatment or prevention of infection or tumor. In addition, the liposomes can be used as supplements of therapeutic agents for infection and tumor.

BACKGROUND OF THE INVENTION

A cellular immune system is one of immune protective mechanisms against invading antigens.

Many means for enhancing cellular immune responses have been known. One example is the administration of agents of stimulating immune cells such as cytokine and the like. Vaccines inducing immune responses specific for infecting antigens also enhance the cellular immune system. Further, Some adjuvants used in combination with vaccines such as LPS enhances non-specific immune responses.

It has been well documented that many agents with strong stimulatory effects on macrophages either contain carbohydrate (e.g. zymosan, LPS) or are chemically similar to carbohydrate (e.g. pyran) (1, 2). Several β-glucans have been shown to stimulate various facets of cellular immune responses. For example, in vitro studies have revealed that β-glucans activate macrophages, neutorphils, and NK cells to kill sensitive tumor cells (2–6) as well as potentiate T cell responses to cellular antigens (7). High molecular weight β-glucans have been shown to stimulate neutrophil degranulation and respiratory bursts (8) and secretion of IL-1, TNF-α, GM-CSF, and IL-6 from macrophages (9, 10). Numerous studies have demonstrated that β-glucans, either soluble or particulate, isolated from various natural sources and wide variable molecular sizes and secondary structures, exhibit antitumor and antimicrobial activities in mouse model system(3, 4, 6, 11). Some of them have been applied clinically for tumor immunotherapy, such as the fungal β-glucan, lentinan and schzophillan (13–16).

The fact that β-glucans which have no significant side-effect and are safe in pharmaceutical use act to enhance a cellular immunity should be noticed in order to treat many types of infection and tumor more effectively. So, there is still necessity to study β-glucans directed to the immune system, especially the enhancement of a cellular immunity.

SUMMARY OF THE INVENTION

Accordingly, an object of the present invention is to obtain a pharmaceutical agent or composition having a higher activity of enhancing a cellular immunity by increasing the activity of enhancing a cellular immunity of the β-glucan mentioned above.

During the studies for attaining the above object, we newly found that a β-glucan encapsulated in liposomes has a higher activity of enhancing a cellular immunity as compared with an unencapsulated β-glucan. According to our studies, liposomes encapsulating a β-glucan show high activity of enhancing a cellular immunity, especially when transmucosally administered.

One aspect of the present invention is liposomes encapsulating a β-glucan which are transmucosally administered to a subject in need of the enhancement of a cellular immunity.

Another aspect of the present invention is a pharmaceutical composition comprising liposomes encapsulating a β-glucan in an effective amount for the enhancement of a cellular immunity, which are administered to a subject in need of said enhancement.

Further aspects of the present invention will be clear from the disclosures herein.

DETAILED EXPLANATION OF THE INVENTION

Figure 1:
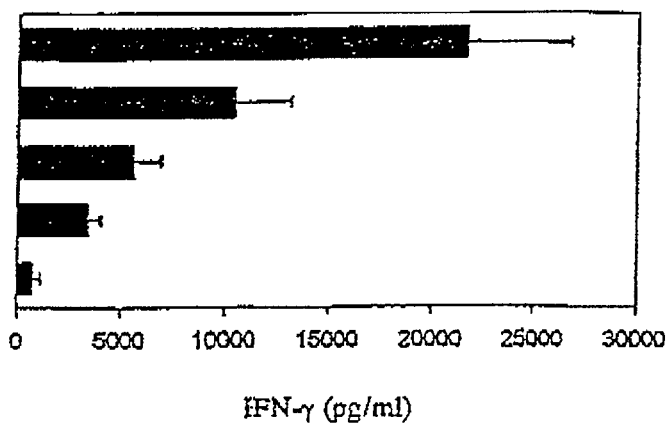
FIG. 1 depicts the results of analysis of HIV env-specific IFN-γ production (A) and serum specific antibodies (B) in orally immunized mice.
Figure 1:
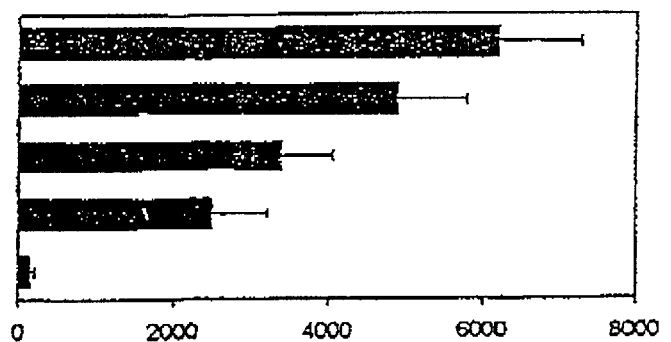

The term "β-glucan" as used herein means a polysaccharide mainly composed of glucose units, wherein bonds between glucose units are mainly β-glycoside bonds. Thus, the β-glucan of the present invention may comprises other saccharides than glucose. It may have α-glycoside bonds between constituent saccharide units. The α- or β-glycoside bond may be, for example, an 1,3-glycoside bond, 1,4-glycoside bond or 1,6-glycoside bond. When each of the saccharide units of the β-glucan has a single binding position, the polysaccharide chain is liner, while if any of the saccharide units of the β-glucan has two binding position such as position 1 and position 6, the polysaccharide chain is branched. The β-glucan of this invention includes both of the branched and liner polysaccharides.

The β-glucan may be a polysaccharide having amino and/or carboxyl groups from any constituent saccharide(s) other than glucose in addition to hydroxy groups from glucose and/or any other constituent saccharide(s), which hydroxyl, amino or carboxyl groups may be acylated, esterified with, for example, sulfuric acid, phosphoric acid or the like, or etherified.

Molecular weight of the β-glucan can be selected from a wide range. Preferable molecular weight thereof is in the range of 1,000 to 2,000,000, more preferably in the range of 5,000 to 1,500,000.

The β-glucan can be obtained from various microorganisms including bacteria, yeasts, basidiomycetes and the like.

Typical known examples of the β-glucan originating from microorganism include curdlan, lentinan, schizophyllan, sclerotan, lutean and succinoglucan. Particularly, curdlan and lentinan are preferable β-glucans.

As is well known in the art, a cellular immunity includes any of immune systems in which a cell or cells are concerned in or mediate immunity, but excludes the immune system in which an antigen is inactivated by an antibody (i.e. humoral immunity).

It is known that various types of liposomes can be obtained depending on methods for their preparation and starting materials used, especially lipid used. Particle size (average) of a liposome population affects the stability and residence time in blood. It also affects an encapsulated amount of a drug (i.e. the β-glucan). In general, liposomes having smaller particle size are monolayered and liposomes having larger particle size are multilayered. Depending on a lipid used, liposomes obtained have a positive or negative charge or are neutral.

Any of the aforementioned liposomes can be used for encapsulating the β-glucan in the present invention. Since the β-glucan is soluble in an aqueous medium, liposomes used in the present invention should be that capable of encapsulating an aqueous medium. Most liposomes can encapsulate an aqueous media. The aqueous medium as used herein means water and any other medium optionally containing other water soluble component such as glycerol and the like.

As methods for the preparation of liposomes, various methods such as a vortex method (Bangham A D et al., Methods Membr. Biol., 1: 1–20, 1974), an ultrasonic treatment method (Johnson S M et al., Biochim. Biophys. Acta, 233: 820–826, 1971), an ethanol injection method (Kremer J M H et al., Biochemistry, 16: 3932–3941, 1980), a french press method (Hamilton et al., J. Lipid Res. 21: 981–982, 1980), a cholic acid removal method (Enoch H G et al., Proc. Natl. Acad. Sci., 76: 145–149, 1979), an ether injection method (Deamer D N, Ann, N.Y. Acad. Sci., 308: 250–258, 1987), a freeze-thaw method (Papahadjopoulos D et al., Biophim. Biophys. Acta, 394: 483–491, 1975) and a reverse phase evaporation method (Szoka F et al., Proc. Natl. Acad. Sci. USA, 75: 4191–4198, 1978) and the like have been known. Their disclosures with respect to the methods for the preparation of liposomes are incorporated by reference herein.

Encapsulation of the β-glucan in liposomes is performed according to any known method. Generally, the β-glucan is encapsulated during the preparation of a liposome as mentioned above. The β-glucan may be encapsulated after the preparation of the liposome by taking advantage of the difference in concentration, the difference in osmotic pressure or the difference in pH, between inner and outer phases of the liposomes.

The liposomes are administered as an aqueous suspension. Such an aqueous suspension of liposomes is defined as "the liposomes" and "the pharmaceutical composition comprising the liposomes" in the present invention.

If necessary, the aqueous suspension of liposomes may contain a saccharide as a stabilizer for the liposomes, such as trehalose, mannose or glucose. An aqueous solvent may be a pH buffer.

The liposomes may be lyophilized and stored. The lyophilized product of liposomes may contain the stabilizer such as a saccharide and the like. Such a lyophilized product and its rehydrate are also included in the definitions of "the liposomes" and "the pharmaceutical composition comprising the liposomes" in the present invention.

The liposomes as well as the pharmaceutical composition comprising the liposomes of the present invention have a high activity of enhancing a cellular immunity. Accordingly, the liposomes as well as the pharmaceutical composition comprising the liposomes of the present invention are administered to a subject in need of the enhancement of a cellular immunity.

The enhancement of cellular immunity is desired in the treatment or prevention of infection or tumor. Thus, the first group of subjects in need of the enhancement of a cellular immunity includes mammals (including human) in need of the treatment or prevention of infection or the treatment of tumor. The above infection means diseases caused by infecting with viruses, bacteria, fungi, parasites or the like. One typical example of the viruses is a human immunodeficiency virus.

The liposomes as well as the pharmaceutical composition comprising the liposomes of the present invention can be used as adjuvants which are used in combination with vaccines (antigens). Thus, the second group of subjects in need of the enhancement of a cellular immunity includes mammals (including human) to which vaccines are administered. In the second group of the subjects, the liposomes or the pharmaceutical composition comprising the liposomes of the present invention may be administered before or after the administration of a vaccine or simultaneously with thereof.

The liposomes or the pharmaceutical composition comprising the liposomes of the present invention will assist the therapy for infection or tumor by medication by enhancing a cellular immunity. Thus, the third group of subjects in need of the enhancement of a cellular immunity includes mammals (including human) to which the therapy for infection or tumor by medication are conducted. In the third group of the subjects, the liposomes or the pharmaceutical composition comprising the liposomes of the present invention are used as an supplement for a therapeutic agent for infection or tumor (principle agent). When the liposomes or the pharmaceutical composition comprising the liposomes of the present invention are used as the supplement, they may be administered before or after the administration of the principle agent or simultaneously with thereof.

Specifically, if a subject is infected with, for example, a human immunodeficiency virus, the liposomes or the pharmaceutical composition comprising the liposomes of the present invention are administered to the subject for the prevention of an onset of AIDS, for the treatment of AIDS, as an adjuvant for an AIDS vaccine, as a supplement of a therapeutic agent for AIDS, or as an agent for the treatment or prevention of AIDS.

According to our studies, transmucosal administration is the most preferred administration route among various administration routes for effectively enhancing a cellular immunity, so far as the liposomes and the pharmaceutical composition comprising the liposomes of the present invention are concerned in the enhancement of a cellular immunity.

The transmucosal administration includes sublingual, intranasal, oral mucosal, inhalation, enteromucosal and transrectal administrations and by suppositories. The preferred enteromucosal administration includes oral administration. Among the above transmucosal administration routes, oral administration is particularly preferable since the oral administration is simple and it does give no stress to the subject.

According to our studies, the β-glucan encapsulated in a liposomes shows a very high migration in blood when orally administered, as compared with that of an unencapsulated β-glucan.

A dose of the liposomes or the pharmaceutical composition comprising the liposomes of the present invention, that is, an effective amount for the enhancement of a cellular immunity is determined by a physician depending on various factors such as sex, age, body weight of a subject to be administered; diet, administration route; conditions and severity; and the like.

When the liposomes or the pharmaceutical composition comprising the liposomes of the present invention are transmucosally administered, the dose in terms of β-glucan is selected from the range of 0.001 mg/kg to 100 mg/kg, preferably the range of 0.02 mg/kg to 10 mg/kg.

The features of the present invention will be clear from the explanation of the following examples. These examples are presented to illustrate the invention and are not to be construed as limiting the scope of the invention.

EXAMPLE

This example demonstrates that when a vaccine comprising HIV envelope (env) glycoprotein gp 160 as an antigen is administered, a β-glucan encapsulated in liposomes has a very high activity of enhancing cellular immunity as compared with that of the unencapsulated β-glucan, and further that the enhancement of cellular immunity is significantly high when a β-glucan encapsulated in liposomes is tranmucosally administered. The gp 160 is administered as a plasmid DNA having DNA encoding gp 160 and as a recombinant vaccinia virus expressing gp 160. As the β-glucan, lentinan is used.

METHODS AND MATERIALS

Lentinan

Lentinan (m.w. −500 kDa) was obtained from Ajinomoto Central laboratories (Kawasaki, Japan). For the in vitro and in vivo studies, lentinan was resuspended in PBS at a final concentration of 2 mg/ml and homogenized for 2.5 min on ice using Branson Sonifter 450 equipped with a ⅛ inch tapered microtip probe and micro tip horn (Branson, 22309796 and NC9406816, respectively) with the following setting: duty cycle 50, output control:7. After incubation on ice, the sonication was repeated for additional 60 sec. This treatment resulted in a homogenous preparation of lentinan with no visible particles. This preparation was used for both in vitro and in vivo stimulation of env-specific immune responses.

Encapsulation of Plasmid DNA-encoding gp160 in PLG Microparticles

Controlled-release microparticles with entrapped plasmid DNA were prepared with a poly (DL-lactide-co-glycolide) (PLG) polymer (Sigma, St. Louis, Mo.) using the water in oil in water solvent evaporation method(20). The env gene segment(19) was cloned in the SmaI and NotI restriction sites of the pCI plasmid (Promega, Medison, Wis.), and encapsulated in PLG microparticles as described(16). Briefly, the polymers had a 50:50 ratio of lactide:glycolide and an inherent viscosity of 0.47 dl/g. 200 mg of PLG dissolved in 6 ml of dichloromethane (Signa) was mixed by vortexing with 0.3 ml of TE buffer (pH 7.4) containing 5 mg of plasmid DNA and sonicated for 1 min (Branson Sonifer 450, Danbury, Conn.). The resulting solution was emulsified in 8% polyvinyl alcohol solution (PVA) (Sigma) using the PowerGen 125 homogenizer (Fisher Scientific, Pittsburgh, Pa.). The emulsion was then poured into 100 ml of 8% PVA and stirred magnetically overnight at room temperature to allow solvent evaporation and microparticle formation. The microparticles were isolated by centrifugation, washed three times in water, and freeze dried. The final product was stored in a desiccator below −20° C. The microsphere size profile was analyzed on a Coulter Counter (Miami, Fla.). DNA integrity was determined by dissolving 25 mg of the PLG microparticles in 500 $\mu$l of chloroform. After adding 500 $\mu$l of water, DNA was extracted by ethanol precipitation and analyzed on an agarose gel. To measure incorporation of DNA, the PLG microparticles were dissolved in 0.1 M NaOH at 100° C. for 10 min, and DNA content was determined by the $A_{260}$ measurement. Incorporation of DNA into microparticles ranged from 1.3 to 2.1 $\mu$g of DNA per mg of PLG.

Vaccinia Viruses

The recombinant vaccinia viruses expressing the full-length $HIV_{HIS}$-1 gp160 (vPE16; 23), and the WR strain of non-recombinant vaccinia virus (vac; 24) were provided by Dr. B. Moss (Laboratories of Viral Diseases, National Institute of Allergy and Infectious Diseases, Bethesda, Md.).

Liposome Preparation

For preparation of vPE16- or lentinan-associated cationic liposomes, a mixture of 1 $\mu$mol of dioleoyl-3-trimethylanonium-propane (DOTAP; Avanti Polar Lipids, Alabaster, Ala.), 1 $\mu$mol of 1,2-dioleoyl-sn-glycero-3-phosphoethanolamine (DOPE; Avanti Polar Lipids) and in some preparations, 0.5 $\mu$mol of 1,2-dilauroyl-sn-glycero-3-phosphocholine (DLPC; Avanti Polar lipids) was dissolved in chlorophorm and placed into a glass pear bottom vial connected to a rotary evaporator (Labconco, Kansas City, Mo.). The lipid solution was thoroughly ventilated using a nitrogen stream (25, 26). Chlorophorm was carefully evaporated under reduced pressure, rotating at 100 rpm to form a lipid film. The lipid film was wetted with 3 ml of PBS containing either the vPE16 vaccinia virus or lentinan, and liposomes were then prepared by intense vortex dispersion and 4 min. sonication. After preparation, the unentrapped material was removed on a BIO-GEL, a 50 m agarose gel (Bio-Rad Laboratories, Hercules, Calif.) column. Morphological examination of liposomes in a Hitachi H7000 Scanning Transmission Electron Microscope (Advanced Biotechnologies Inc., Columbia, Md.), revealed multilamellar structures of the vesicles with distinct striated organization. The titer of the vPE16 virus complexed with liposomes was determined by plating serial 10-fold dilutions on a plate of human HuTK143B indicator cells, staining with crystal violet and counting plaques at each dilution. The concentration of lentinan encapsulated in liposomes was determined using the Fungitec G test (Seikagaku Co., Japan) according to the manufacturer's protocol.

Oral Vaccination

Female BALB/c (H-2 d) mice were purchased from the Jackson Laboratory (Bar Harbor, Me.) and were maintained in a specific pathogen-free microisolator environment. Mice were immunized three times (on days 0, 7, and 14) with PLG-encapsulated plasmid DNA delivered orally using a 24-gauge feeding needle (Popper & Sons, Inc., New Hyde Park, N.Y.). For a booster immunization with the live vector, mice primed with the DNA vaccine received orally $10^7$ PFU of the vPE16 vaccinia virus or liposome-associated vPE16. Lentinan-encapsulated in liposomes was delivered on a daily basis during entire the immunization period, Control mice received orally PLG-encapsulated pCI plasmid and vac-associated liposomes or liposomes with PBS instead of lentinan.

Quantification of Lentinan in Serum After Oral Administration

Formulations of 400 μg of lentinan dissolved in PBS or associated with liposomes were delivered orally in four doses to fasted mice over a period of 4 hrs. The level of lentinan in blood serum was measured 2 hr after the delivery using the Fungitec G test (Seikagaku Co., Inc.), according to the manufacturer's protocol. Background activity was determined by analyzing lentinan levels in sera of control mice.

Cell Purification

Induction of env-specific Th1 and CTL -responses in Peyer's patches, lamina propria, and spleen were analyzed three weeks after the third immunization. Lymphocytes from lamina propria were dissociated into single cells by enzymatic digestion as described (27). Briefly, the large and small intestines were dissected from individual mice and the mesenteric and connective tissues carefully removed. Fecal material was flushed from the lumen with medium. After the Peyer's patches were identified and removed from the intestinal wall, the intestines were opened longitudinally, cut into short segments, and washed extensively in complete medium. To remove the epitheial cell layer, tissues were placed into 20 ml of 1 mM EDTA and incubated twice (for 40 min and then for 20 min) at 37° C. with stirring. After the EDTA treatment, tissues were washed in complete medium for 10 min, placed into 50 ml of RPMI 1640 medium containing 10% FCS and incubated for 15 min at 37° C. with stirring. To isolate lamina propria lymphocytes, tissues were cut into small pieces and incubated in medium containing collagenase type VIII, 300 units/ml (Sigma) for 50 min at 37° C. with stirring. This collagenase dissociation procedure was repeated two times and the isolated cells pooled and washed again. To remove dead cells and tissue debris, cells were passed through a cotton-glass wool column (Fisher Scientific) and then layered onto a discontinuous gradient containing 75% and 40% Percoll (Sigma). After 20 min centrifugation (600×g) at 4° C., the interface layer between the 75% and 40% Percoll was carefully removed and washed with medium. This procedure provided over 95% viable lymphocytes with a cell yield of $1.5-2 \times 10^6$ lymphocytes per mouse. Spleen cells were aseptically removed and single cell suspension prepared by gently teasing the cells through sterile screens.

In vitro Stimulation Assay

Lymphocytes from spleen ($3 \times 10^6$ cells/ml), Peyer's patches and lamina propria ($2 \times 10^5$ cells/ml) were incubated in 96-well plate (Linbro, ICN Biomedicals, Inc., Aurora, Ohio) with 3 μg/ml of rgp160 (Immunodiagnostics Inc., Bedford, Mass.) or medium only. On the third day of simulation, culture supernatants were collected and analyzed for IFN-γ production by the ELISA assay (Quantikine™, R&D Systems, Minneapolis, Minn.) according to the manufacturer's protocol.

Anti-gp160 Antibody ELISA

A direct ELISA assay was used to determine the presence of env-specific antibodies in serum and fecal washes. Ninety-six-well Maxisorp ELISA plates (Nunc, Naperville, Ill.) were coated overnight at 4° C. with 100 μl of 3 μg/ml rgp160 as described (28). The rest of the ELISA assay was conducted at room temperature. Following a wash with PBS containing 0.05% Tween-20 (PBS/Tween-20), the wells were blocked for 2 h with a solution containing 2% BSA (Sigma) and 0.05% Tween-20 in PBS. Sera were prepared from murine blood samples, serially diluted in PBS/Tween-20 and added to ELISA wells. After incubation at room temperature for 1 h, the plate was washed three times and then incubated with a 1/10,000 dilution of a peroxidase-conjugated goat anti-mouse Ig (IgG, IgM, and TgA; Sigma) in PBS/Tween. The plates were washed 3 times and developed with O-phenylenedianine (0.4 mg/ml; Sigma) in 0.05M phosphate-citrate buffer containing 0.03% sodium perborate (Sigma), stopped with 0.4 M sulfuric acid, and analyzed at 450 nm with an ELISA plate reader (Dynatech MRX, Chantilly, Va.). Sample dilutions were considered positive if the optical density recorded for that dilution was at least two fold higher than the optical density recorded for a naive sample at the same dilution(29).

The presence of env-specific IgA in fecal samples was measured by ELISA using 1/1,000 dilution of peroxidase conjugated-goat anti-mouse IgA (Sigma). Fecal washes were prepared from fecal samples as described (29). Briefly, fresh fecal samples (100 mg) were mixed with 1 ml of PBS, incubated at room temperature for 15 min, vortexed, and centrifuged in a microcentrifuge for 10 min. Supernatants were collected and stored at −20° C. until assayed for anti-gp160 antibodies.

CTL Assay

Lymphocytes from spleen were cultured at $2 \times 10^6$ cells/ml in 24-well culture plates with medium containing 1 μM of the env peptide I10 (RGPGRAFVTI, amino acids 318–327) (30) and 10% T cell stimulatory factor (T-STIM™ Culture Supplement, Collaborative Biomedical products, Bedford, Mass.) as a source of exogenous IL-2. After three days of stimulation, cells were split and cultured in medium supplemented with 0.3 ng/ml of recombinant mouse IL-2 (Pharmingen, San Diego, Calif.). Cytolytic activity of CTL lines was analyzed after 6 days of cultures by a standard 4 h $^{51}$Cr release assay against 17Cu cells (provided by Dr. M. Wysocks, The Wistar Institute, Philadelphia, Pa.) infected with vPE16 or vac. The percent specific lysis was calculated as: ([cpm experimental release−cpm spontaneous release]/ [cpm maximum release−cpm spontaneous release])×100. Maximum release was determined from supernatants of cells that were lyzed by addition of 5% Triton X-100. Spontaneous release was determined from target cells incubated with medium only.

Analysis of HIV Env-specific IFN-γ Production and Serum Specific Antibodies Induced By Oral Immunization The oral immunization was conducted with env-encoded plasmid DNA (pCI) encapsulated in PLG microparticles, vPE16, and the prime-boost strategy with PLG-encapsulated plasmid DNA encoding gp 160 and vPE16, or liposome-associated vPE16.

Splenocytes from control and immunized mice were stimulated for three days with 3 μg/ml of rgp160. The levels of IFN-γ in cell-free culture supernatants were determined by the ELISA assay. Background values from unstimulated cultures detected for IFN-γ were subtracted from all values given (FIG. 1A).

Sera prepared from murine blood samples were serially diluted and analyzed for gp160-specific antibody responses by ELISA on plates coated with rgp160. For gp120-specific ELISA, sample dilutions were considered positive if the optical density recorded for that dilution was at least two fold higher than the optical density recorded for a naive sample at the same dilution. Significant differences in antibody titers were detected between mice immunized with the env-encoded plasmid DNA versus those immunized by the prime-boost combination with the DNA vaccine and vPE16 (P=0.048) or liposome-associated vPE16 (P=0.001). Results are presented as the mean values±SD of four mice per group (FIG. 1B).

Analysis of HIV Env-specific Mucosal IFN-γ and IgA Responses in Orally Immunized Mice Mice were orally immunized with the env-encoded DNA vaccine alone or in combination with vPE16, or liposome-associated vPE16.

Figure 2:
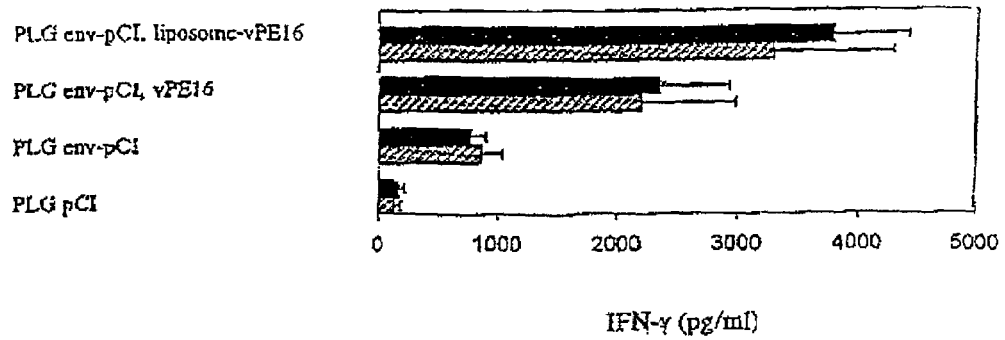
FIG. 2 depicts the results of analysis of HIV env-specific mucosal IFN-γ (A) and IgA (B) responses in orally immunized mice. Hatched bars depict the results of experiments using Peyer's patches, and solid bars depict the results of experiments using lamina propria.
Figure 2:
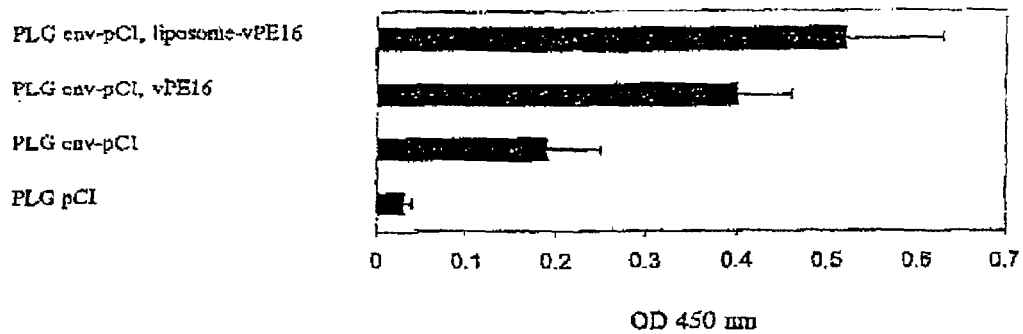

Cells isolated from Peyer's patches and lamina propria were simulated for three days with 3 µg/ml of rgp160, and levels of IFN-γ in cell-free culture supernatants were determined by the ELISA assay. Background values from unstimulated cultures detected for IFN-γ were subtracted from all values given (FIG. 2A).

The levels of env-specific IgA in fecal wash samples were determined by ELISA on plates coated with rgp160. Results are presented as the mean values±SD of four mice per group (FIG. 2B).

Effect of Lentinan on Env-specific IFN-γ Production in Cultures Stimulated with rgp160

Figure 3:
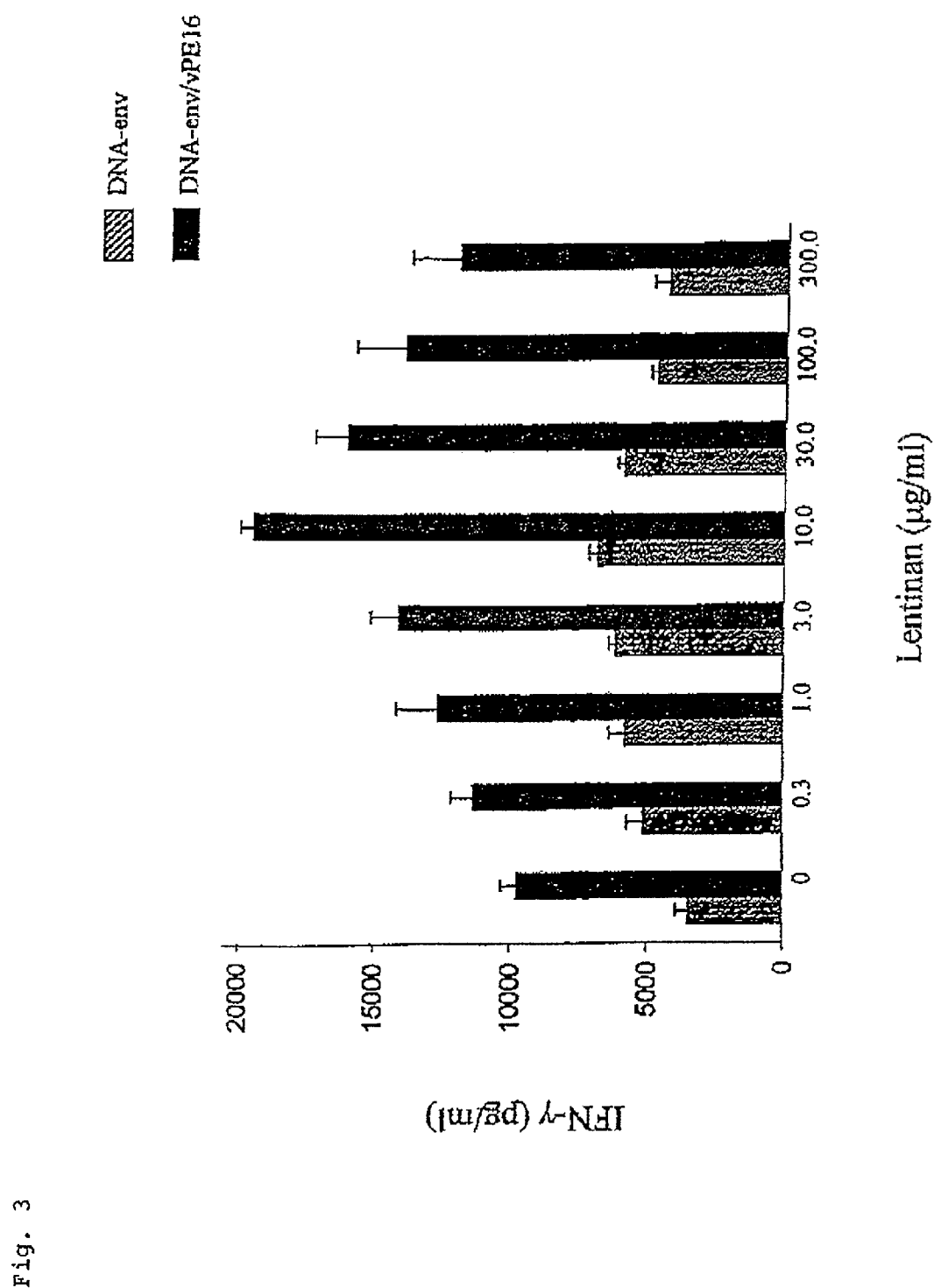
FIG. 3. depicts the results of analysis of effect of lentinan on env-specific IFN-γ production in cultures stimulated with rgp160. Hatched bars depict the results of immunization with PLG-encapsulated DNA encoding gp160, while black bars depict the results of immunization with vPE16 vaccinia virus.

Splenocytes derived from BALB/c mice immunized with PLG-encapsulated DNA encoding gp160 or the DNA vaccine and the vPE16 vaccinia virus were stimulated for three days with 3 µg/ml of rgp160 in the presence various concentrations of lentinan. The level of IFN-γ in cell-free culture supernatants were determined by the ELISA assay. Background values from unstimulated cultures were subtracted from all values given. Results are presented as mean values±SD of five independent experiments (FIG. 3).

Figure 4:
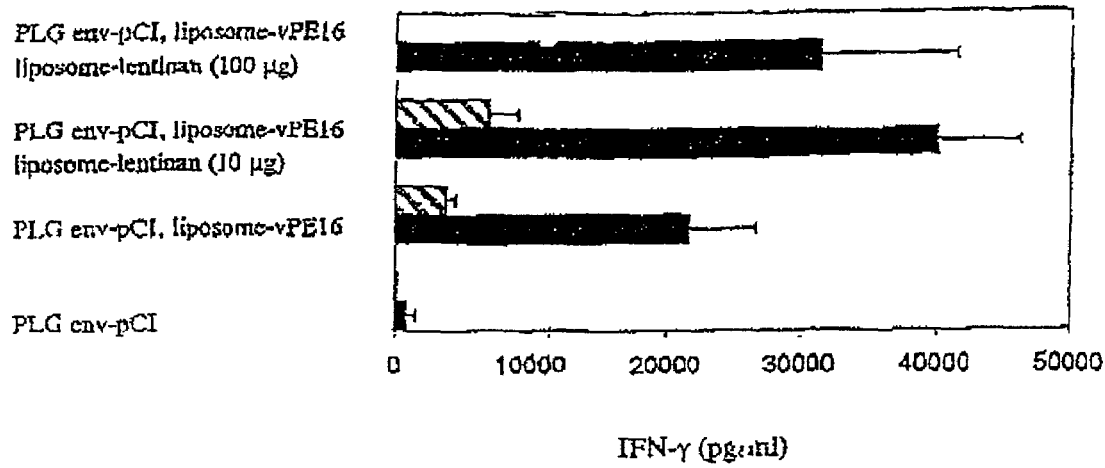
FIG. 4 depicts the results of analysis of effect of lentinan on env-specific IFN-γ production (A) and serum antibody responses (B) in orally immunized mice. Solid bars depict the results of experiments using splenocytes, while hatched bar depict the results of experiments using lamina propria.
Figure 4:
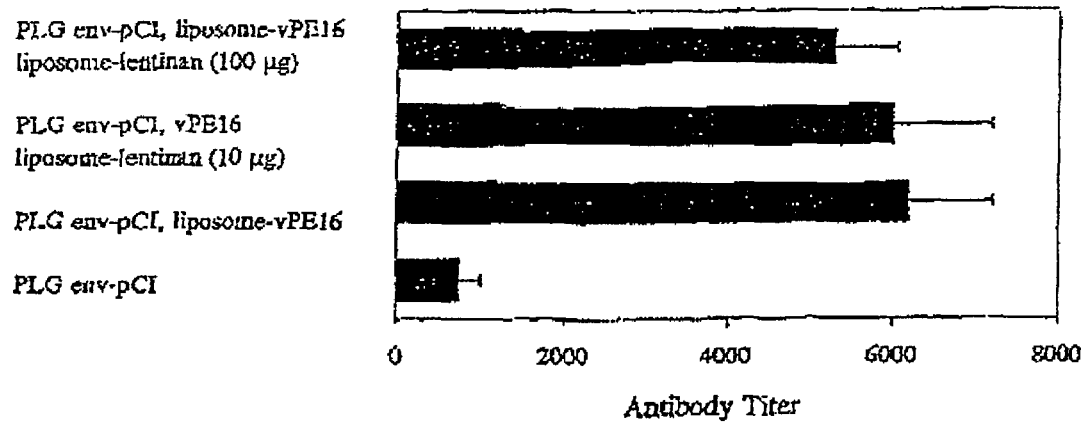

Effect of Lentinan on Env-specific IFN-γ Production and Serum Antibody Responses in Orally Immunized Mice Lentinan was encapsulated in liposomes and delivered daily in doses of 10 and 100 µg during the entire immunization period. The level of IFN-γ production in rgp160-stimulated cultures established from splenocytes and lymphocytes isolated from lamina propria was determined by the ELISA assay (FIG. 4A). The serum env-specific antibody responses were analyzed on plates coated with rgp160 (FIG. 4B).

Induction of Env-specific CTL Responses by Intragastric Immunization

Figure 5:
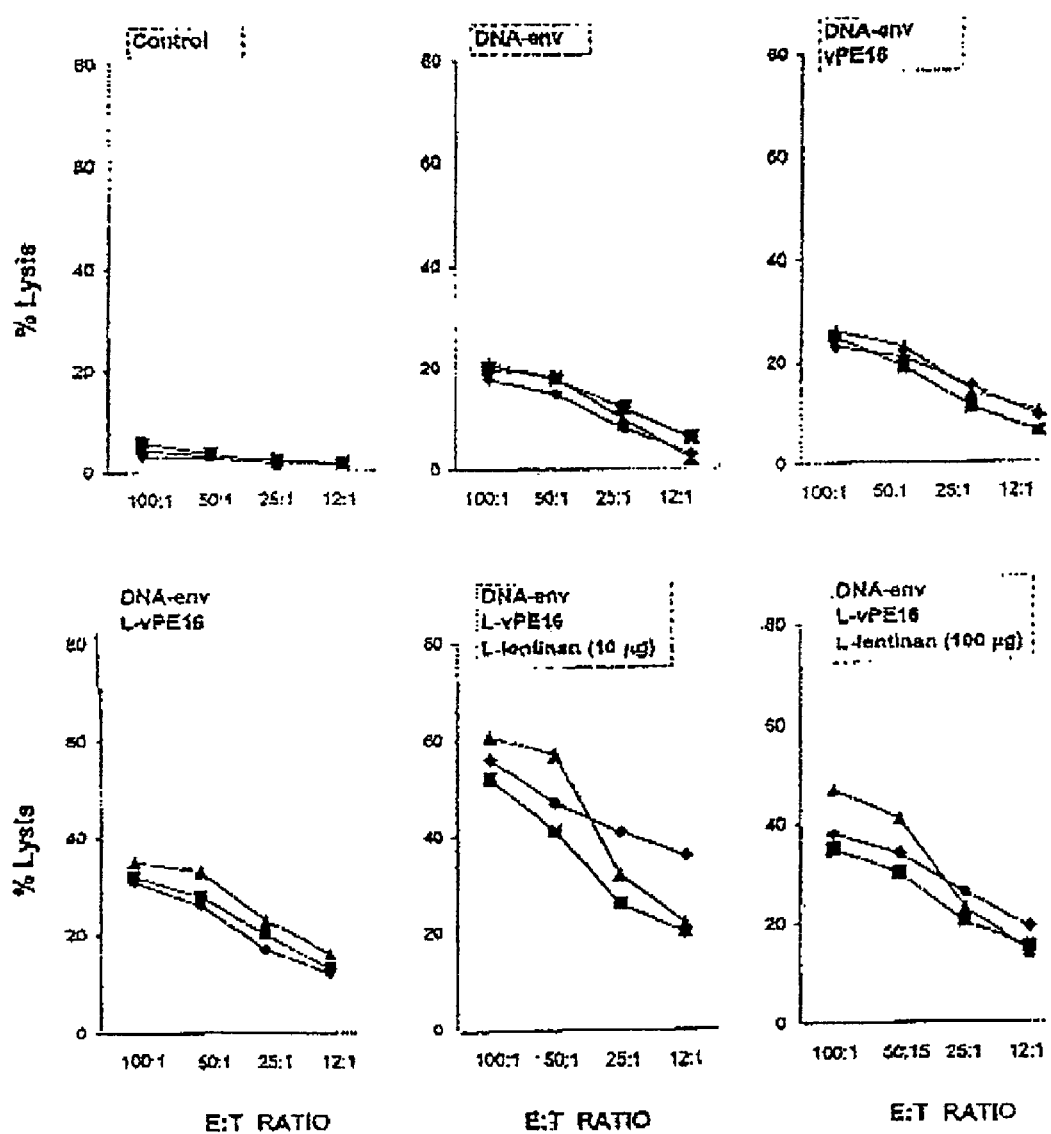
FIG. 5 depicts the results of induction experiments of env-specific CTL responses by intragastric immunization with genetic vaccines in the presence or absence of lentinan.

Lymphocytes derived from spleen were stimulated with the I10 peptides for six days in the presence of murine recombinant IL-2. The env-specific CTL responses were analyzed by $^{51}$Cr-release assay in bulk cultures against vPE16-infected 17Cu cells. The percent of lysis with vac-infected cells used a negative control were subtracted from the presented values. All CTL experiments were run in triplicate with SD<10% (FIG. 5).

Results

Systemic Env-specific IFN-γ and Antibody Responses Induced by Prime-boost Immunization Strategies with PLG-encapsulated DNA Plasmid Encoding gp160 and vPE16

In the initial experiments we have explored strategies for optimizing the efficacy of orally delivered genetic vaccines. Because oral vaccines have most frequently been delivered in a form of PLG-encapsulated plasmid DNA (17–20) or recombinant viruses (21–22), we first compared levels of env-specific immune responses in mice immunized orally with PLG-encapsulated plasmid DNA encoding gp160 and vPE16 administered alone or in a prime-boost combination Analysis of IFN-γ production in cell-free supernatants of rgp160-stimulated splenocytes revealed the highest levels of IFN-γ responses in cultures established from mice immunized with the prime-boost combination (11,000±2,330 pg/ml; FIG. 1A). The levels of env-specific IFN-γ production in mice that received env-encoded DNA plasmid followed by vPE16 booster were 2- to 3-fold higher than IFN-γ responses detected after immunization with each of the vector delivered alone. Association of vPE16 with liposomes during the oral delivery further enhanced env-specific IFN-γ production (19,500±3,605 pg/ml).

In parallel experiments, we have examined induction of env-specific antibodies in sera of the immunized mice (FIG. 1B). Detectable env-specific antibody responses were measured in animals immunized orally with PLG-encapsulated plasmid DNA encoding gp160 (titer: 2,500±720) and vPE16 (titer: 3,400±650). The antibody titer increased approximately twice (6,200±1,100) in mice immunized with the prime-boost combination. The booster immunization with liposome-associated vPE16 increased the level of env-specific serum antibodies as compared with that induced by vaccination with the free virus although the increases were less than those seen with env-specific IFN-γ responses. Results of these experiments demonstrated that the delivery system based on intragastric administration of PLG-encapsulated plasmid DNA followed by liposome-associated recombinant viral vector represents a viable means for induction of env-specific immune responses.

Env-specific Mucosal IFN-γ and Antibody Responses

Previous studies have shown the presence of env-specific immune responses in mucosal tissues of gut after oral administration of PLG-encapsulated DNA plasmid encoding gp160 (17–20) or after immunization with the vPE16 vaccinia virus (21, 22). To analyze whether a delivery system based on the combination of these two approaches would enhance levels of env-specific mucosal immunity, we examined env-specific IFN-γ production in rgp160-stimulated cultures established from lymphocytes isolated from Peyer's patches and lamina propria. Consistent with the level of env-specific responses in spleen, the highest production of env-specific IFN-γ was measured in cultures established after a prime-boost immunization with PLG-encapsulated plasmid DNA encoding gp160 followed by liposome-associated VPE16 (FIG. 2A). Similarly, mucosal IgA responses directed to the env glycoprotein were highest in fecal washes of mice vaccinated orally with the same prime-boost immunization strategy (FIG. 2B).

Induction of IFN-γ Production by Lentinan in vitro

In the initial experiments, we examined the effect of lentinan on the level of env-specific IFN-γ production during in vitro stimulation with rgp160. Splenocytes were isolated from mice immunized orally with PLG-encapsulated plasmid DNA encoding gp160 alone or from animals that received the prime-boost combination of the DNA vaccine and vPE16. The cells were stimulated with rgp160 in the presence of various concentrations of lentinan for 3 days, and the level of env-specific IFN-γ production was determined in cell-free supernatants by the ELISA assay. As shown in FIG. 3, the presence of lentinan during stimulation enhanced the level of env-specific IFN-γ responses in a dose dependent manner. The highest increases in env-specific IFN-γ production were mediated by lentinan at concentrations ranging from 3 µg/ml to 100 µg/ml. In these cultures, levels IFN-γ were ~2-fold higher as compared with those induced by stimulation with rgp160 in the absence of lentinan. Concentrations of lentinan higher than 100 µg/ml or lower than 3 µg/ml had smaller effect on env-specific IFN-γ production. Results of these studies demonstrated that lentinan was capable of augmenting env-specific IFN-γ production in vitro within a relatively broad range of concentrations and without any detectable toxic effect to the cells.

Effect of Lentinan on Env-specific IFN-γ and Antibody Responses

We first investigated whether lentinan dissolved in PBS or associated with liposomes would penetrate through the epithelial barrier of the gut. Mice were fed with four doses of liposome-associated or unencapsulated lentinan (total concentration of 400 μg) over a 4-hr period. The level of lentinan in blood serum was analyzed 2 hr after lentinan administration. As shown in Table 1, association of lentinan with liposomes facilitated uptake of this high m.w. β-glucan in the gastrointestinal track. Mice fed with this formulation of lentinan demonstrated detectable levels of lentinan in the serum at concentrations that varied between 4,649 pg/ml to 8,885 pg/ml. In contrast, oral delivery of the unencapsulated lentinan resulted in a serum level of this compound similar to that measured in the control group of mice (1,325±1,241 pg/ml versus 215±527 pg/ml, respectively). Results of these experiments demonstrated that lentinan once associated with liposomes could penetrate the intestinal epithelium and be transferred to the circulation.

TABLE I

Quantification of lentinan in blood sera of mice fed with liposome-associated or unencapsulated lentinan.

| Group* | Lentinan formulation | Serum concentration of lentinan (pg/ml) |
| --- | --- | --- |
| I | PBS | 215 ± 527 |
| II | Unencapsulated lentinan | 1,325 ± 1,241 |
| III | Liposome-associated lentinan | 6,422 ± 2,287 |

Mice were fed four times with 100 μg of free or liposome-associated lentinan during a 4-hr period. The level of lentinan in blood sera was analyzed 2 hr after the last administration of lentinan. The concentration of lentinan in blood sera was determined by the Fungitec G test. Significant differences (P = 0.0005) in serum concentration on lentinan were detected between mice fed with unencapsulated and liposome-associated lentinan.

For the adjuvant activity study in vivo, lentinan was encapsulated in liposomes and delivered daily in doses of 10 and 100 μg during the immunization period with PLG-encapsulated plasmid DNA encoding gp160 and liposome-associated vPE16. In the first set of experiments, we examined the effect of lentinan on levels of env-specific IFN-γ production in rgp160-stimulated cultures established from spleen and lamina propria of the immunized mice. The analysis revealed an increased level of IFN-γ in rgp160-stimulated cultures established from mice fed daily with 10 μg of cultures established from mice fed daily with 10 μg of lentinan-associated with liposomes (FIG. 4A). In splenocytes, the production of TFN-γ ranged from 38,000 pg/ml to 44,000 pg/ml, and was ~2-fold higher than levels of IFN-γ induced by immunization in the absence of lentinan (P=0.028). A similar pattern of responses was detected in rgp160-stimulated cultures established from lymphocytes isolated from lamina propria of the immunized mice (FIG. 4A). Although 100 μg of lentinan encapsulated in liposomes also augmented env-specific IFN-γ responses (P=0.05), the increases were less than those induced with 10 μg of liposome-encapsulated lentinan. In contrast to the enhancing effect on IFN-γ production, lentinan did not augment the level of env-specific serum antibodies (FIG. 4B).

Lentinan-associated Increases in Env-specific CTL Responses

To determine whether the adjuvant effect of lentinan on evn-specific IFN-γ production after oral immunization with PLG-encapsulated plasmid DNA and liposome-associated vPE16 could also be reflected in higher cytotoxic responses, we compared levels of env-specific CTL activities in spleen obtained from mice immunized with different vaccine combinations. Splenocytes derived from immunized and control mice were stimulated with the env-specific, H-2d -restricted peptide I10 for 6 days and the level of env-specific CTL responses were determined using a standard $^{51}$Cr-release assay. The CTL activities in I10-stimulated cultures were analyzed against 17Cu cells (a clone derived from the H-2d-positive 3T3 fibroblasts) infected with vPE16. In parallel, each culture was analyzed for CTL responses against 17Cu cells infected with the non-recombinant vaccinia virus(vac) as a negative control.

Consisted with profile of rgp160-induced IFN-γ responses, the oral prime-boost immunization with PLG-encapsulated plasmid DNA and liposome-associated vPE16 induced higher levels of env-specific CTL activities than those detected after the DNA vaccine or the DNA vaccine-vPE16 prime-boost combination. As shown in FIG. 5, the CTL activity against vPE16-infected ranged from 18% to 21% specific lysis at the E:T ratio of 50:1 in mice immunized orally with PLC-encapsulated plasmid DNA encoding gp160. The env-specific CTL responses were enhanced by the booster vaccination with vPE16 and after oral delivery of liposome-associated lentinan, reaching the level of ~30% specific lysis at the E:T ratio of 50:1. The oral administration of liposome-associated lentinan during the immunization period further enhanced the CTL responses. The highest env-specific CTL activity was detected in I10 peptide-stimulated cultures established from the immunized mice treated with 10 μg of lentinan encapsulated in liposomes. In these cultures, levels of env-specific CTL activity varied between 42% and 58% specific lysis at the E:T ratio of 50:1, and were consistently higher than those measured in cultures established from mice treated with 100 μg of liposome-associated lentinan.

REFERENCES

1. Vetvicka, V., B. P. Thornton, T. J. Wieman, and G. D. Ross. 1997. Targeting of natural killer cells to mammary carcinom via naturally occurring tumor cell-bound iC3b/ and β-glucan-primed CR3(CD11b/CD18). J. Immunol. 159:599.
2. Vetvicka, V., B. P. Thornton, and G. Ross. 1996. Soluble β-glucan polysaccharide binding to the lectin site of neutrophil or natural killer cell complement receptor type 3 (CD11b/CD18) generates a primed state of the receptor capable of mediating cytotoxicity of iC3b-opsonized target cells. J. Clin. Invest. 98:50.
3. Diller, I. C., Z. T. Mankowski, and M. E. Fisher. 1963. The effect of yeast polysaccharides on mouse tumors. Cancer, Res. 23:201.
4. Di Luzio, N. R., D. L. Williams, R. B. McNamee, B. F. Edwards, and A. Kitahama. 1979. Comparative tumor-inhibitory and anti-bacterial activity of soluble and particulate glucan. Int. J. Cancer. 24:773.
5. Seljelid, R., J. Bogwals, J. Hoffman, and O. Larm. 1984. A soluble β-1,3-D-glucan derivative potentiates the cytostatic and cytolytic capacity of mouse peritoneal macrophages in vitro. Immunopharmacology 7:69.

6. Morikawa, K., T. Noguchi, M. Yamazaki, and D. Mizuno. 1986. Calcium-dependent and -independent tumoricidal activities of polymorphonuclear leukocytes induced by a linear β-1,3-D-glucan and phorbol myristate acetate in mice, Cancer Res. 46:66.

7. Hamuro, J., M. Rollinghoff, and H. Wagner. 1978. β(1–3) glucan-mediated augmentation of alloreactive murine cytotoxic T lymphocytes in vivo. Cancer Res. 38:3080.

8. Ross, G. D. 1993. Membrane complement receptors. In Clinical Aspects of Immunology. P. J. Lachmann, D. K. Peters, F. S. Rosen, and M. J. Walport, editors. Blackwell Scientific Publications. Oxford 241–264.

9. Estrada, A., C-H Yun, A. Van Kessel, B. Li, S. Hauta, and B. Laarveld. 1997. Immunomodulatory activities of oat β-glucan in vitro and in vivo. Microbiol. Immunol. 41:991.

10. Matsuoka, H., Y. Seo, H. Wakasugi, T. Saito, and H. Tomada. 1997. Lentinan potentiates immunity and prolongs the survival time of some patients. Anticancer Research 17:2751.

11. Kaneko, Y., and G. Chihara. 1992. Potentiation of host resistance against microbial infections by lentinan and its related polysaccharides. Microbial Infections. Ed. H. Friedman, T. W. Klein, and H. Yamaguchi, eds. Plenum Press, New York, 201–215.

12. Vetvicka, V., B. P. Thornton, T. J. Wieman, and G. D. Ross. 1997. Targeting of natural killer cells to mammary carcinom via naturally occuring tumor cell-bound iC3b and β-glucan-primed CR3 (CD11b/CD18), J. Immunol. 159:599.

13. Chihara, G. Lentinan and its related polysaccharides as host defense potentiators: their application to infectious diseases and cancer. In Immunotherapeutic Prospects of Infectious Diseases. K. N. Masihi and W. Lange, eds. Springer-Verlag, Berlin, P. 9, 1990.

14. Taguchi, T., H. Furue, T. Kimura, T. Kondo, T. Hattori, and N. Ogawa. 1983. Clinical efficacy of lentinan on neoplastic diseases. Adv. Exp. Med. Biol. 166:181.

15. Tari, K., I. Satake, K. Nakagomi, K. Ozawa, F. Oowada, Y. Higashi, T. Negishi, T. Yamada, H. Saito, and K. Yoshida. 1994. Effect of lentinan for advanced prostate carcinoma, Acta Urol. Jpn. 40:119.

16. Fujimoto. S., H. Furue, T. Kimura, T Kondo, K. Orita, T. Takuchi, K. Yoshida, and N. Ogawa. 1984. Clinical evaluation of schizophyllan adjuvant immunotheraphy for patients with respectable gastric cancer: a randomized controlled trial. Jpn. J. Surg. 14:286.

17. Jones, D. H., Corris, S., McDonald, S. Clegg, J. C. S., and Farrar, G. H. 1997, Poly(DL-lactide-co-glycolide)-encapsulated plasmid DNA elicits systemic and mucosal antibody responses to encoded protein after oral administration. Vaccine 15:814.

18. Chen, S. C., Jones, D. H., Fynan, E. F. Farrar, G. H., Clegg, J. C. S., Greenberg, H. B., and Herrmann, J. E. 1998. Protective immunity induced by oral immunization with a rotavirus DNA vaccine encapsulated in microparticles. J. Virol. 72:5757.

19. Kaneko H., Wierzbicki A., Kiszka, I., Dinochowski, M., Wasik T. J., Kaneko Y., Kozbor D. 2000. Oral administration of DNA vaccine promotes mucosal and systemic cellular responses against HIV envelope glycoprotein. Virology 267:8.

20. Hedley, M. L., J. Curley, J., and R. Urban. 1998. Microspheres containing plasmid-encoded antigens elicit cytotoxic T-cell responses. Nat. Med. 4:365–368.

21. Bender, B. S., C. A. Rowe, S. F. Taylor, L. S. Wyatt, B. Moss, and A. P. Small. 1996. Oral immunization with a replication deficient recombinant vaccinia virus protects mice against influenza. J. Virol. 9:6418.

22. Gherardi, M. M. and M. Esteban. 1999. Mucosal and systemic immune responses after oral delivery of vaccinia virus recombinants. Vaccine 17:1074.

23. Earl, P. L., S. Koenig, and B. Moss. 1991. Biological and immunological properties of human immunodeficiency virus type 1 envelope glycoprotein. Analysis of proteins with truncations and deletions expressed by recombinant vaccinia viruses. J. Virol. 65:311.

24. Mackett, M., G. L. Smith, and B. Moss. 1982. Vaccinia virus: A Selectable eukaryotic cloning and expression vector. Proc. Natl. Acad. Sci. USA 79:7415–7419. Moss, B., G. L. Smith, J. L. Gerin, R. H. Purcell. 1984. Live recombinant vaccinia virus protects chimpanzees against hepaptitis B. Nature 311:67.

25. Gregoriadis, G. and B. E. Ryman. 1972. Fate of protein-containing liposomes injected into rats. Eur J. Biochem, 24:485.

26. Flegner, P. L., Y. J. Isai, J. Marshall, S. H. Cheng, L. Sukhu, C. J. Wheeler, and M. Manthorpe. 1996. Improved cationic lipid formulations for in vivo gene therapy. Ann. N.Y. Acad. Sci. 772:125.

27. Belyakov, I. M., M. A. Derby, J. D. Ahlers, B. L. Kelsall, P. Earl, B. Moss, W. Strober, and J. A. Berzofsky, 1998. Mucosal immunization with HIV-1 peptide vaccine induces mucosal and systemic cytotoxic T lymphocytes and protective immunity in mice against intrarectal recombinant HIV-vaccinia challenge. Proc. Natl. Acad. Sci. USA 95:1709.

28. Barouch, D. H., Santra, S., Steenbeke, T. D., Zheng, X. X., Perry H. C., Davies, M. E., Freed, D. C., Craiu, A. Strom, T. B., Shiver, J. W., and Letvin, N. L. 1998. Augmentation and suppression of immune responses to an HIV-1 DNA vaccine by plasmid cytokine/Ig administration. J. Immunol. 161:1875.

29. Staats, H. F., W. G. Nichols, and T. J. Palker. 1996 Mucosal imnunity to HIV-1; Systemic and vaginal antibody responses after intranasal immunization with the HIV-1 C4/V3 peptide TISP10MN(A). J. Immunol. 157:462.

30. Takahashi, H., Y. Nakagawa, G. R. Leggatt, Y. Ishida, T. Saito, K. Yokomuro, and J. A. Berzofsky. 1996. Inactivation of human immunodeficiency virus (HIV)-1 envelope-specific $CD8^+$ cytotoxic T lymphocytes by free antigenic peptide: A self-veto mechanism? J. Exp. Med. 183:879.

What is claimed is:

1. A method for treating HIV infection in a subject, comprising orally administering a beta-glucan encapsulated in a liposome to said subject in an amount effective to treat HIV infection, wherein the vesicles of said liposome have a multilamellar structure with distinct striated organization.

2. The method of 1, wherein the beta-glucan encapsulated in a liposome is admixed with an transmucosally acceptable carrier.

3. The method of claim 1 wherein the beta-glucan is lentinan or curdlan.

4. The method of claim 1, wherein the beta-glucan is lentinan.

5. The method of claim 1 wherein the beta-glucan is curdlan.

6. The method of claim 1 wherein the molecular weight of the beta-glucan is from 1,000 to 2,000,000.

7. The method of claim 1 wherein the molecular weight of the beta-glucan is from 5,000 to 1,500,000.

8. The method of claim 1 further comprising administering an HIV vaccine to said subject.

9. The method of claim 8, wherein said HIV vaccine is administered before the beta-glucan encapsulated in a liposome.

10. The method of claim 8, wherein said HIV vaccine is administered after the beta-glucan encapsulated in a liposome.

11. The method of claim 8, wherein said HIV vaccine and beta-glucan encapsulated in a liposome are administered simultaneously.

12. The method of claim 1 wherein said effective amount is from 0.001 mg/kg of the subject to 100 mg/kg of the subject.

13. The method of claim 1 wherein said effective amount is from 0.2 mg/kg of the subject to 10 mg/kg of the subject.

* * * * *